United States Patent
Nolan et al.

(10) Patent No.: US 6,369,265 B1
(45) Date of Patent: Apr. 9, 2002

(54) USE OF A CATALYST SYSTEM COMPRISING NICKEL, PALLADIUM, OR PLATINUM AND IMIDAZOLINE-2-YLIDENE OR IMIDAZOLIDINE-2-YLIDENE IN KUMADA COUPLING REACTIONS

(75) Inventors: Steven P. Nolan, New Orleans, LA (US); Jinkun Huang, Des Plaines, IL (US); Mark L. Trudell, Metairie; Chunming Zhang, New Orleans, both of LA (US)

(73) Assignee: University of New Orleans Research & Technology Foundation, New Orleans, LA (US)

( * ) Notice: Subject to any disclaimer, the term of this patent is extended or adjusted under 35 U.S.C. 154(b) by 0 days.

(21) Appl. No.: 09/511,122

(22) Filed: Feb. 22, 2000

Related U.S. Application Data

(60) Provisional application No. 60/154,260, filed on Sep. 16, 1999.

(51) Int. Cl.[7] .......................... C07C 69/76; C07C 2/02; C07C 15/40; C07C 37/00

(52) U.S. Cl. ....................... 560/102; 568/631; 568/797; 585/427; 585/435; 585/457

(58) Field of Search .................... 548/103; 560/102; 568/631, 797; 585/427, 435, 457

(56) References Cited

U.S. PATENT DOCUMENTS

| | | | |
|---|---|---|---|
| 5,077,414 A | 12/1991 | Arduengo, III | 548/335 |
| 5,104,993 A | 4/1992 | Arduengo, III | 548/317 |
| 5,703,269 A | 12/1997 | Hermann et al. | 560/19 |
| 5,728,839 A | 3/1998 | Hermann et al. | 548/103 |

OTHER PUBLICATIONS

Arduengo, III, et al., "Electronic Stabilization of Nucleophilic Carbenes", J. Am. Chem. Soc., 1992, vol. 114, No. 14, ppg. 5530–5534.
Arduengo, III et al., "A Stable Diaminocarbene", J. Am. Chem. Soc., 1995, vol. 117, No. 44, ppg. 11027–11028.
Herrmann, et al., "Metal Complexes of N–Hetercyclic Carbenes—A New Structural Principle for Catalysts in Homogeneous Catalysis", Angew Chem. Int. Ed.Engl., 1995, vol. 34, No. 21, ppg. 2371–2374.
Herrmann, et al., "N–Heterocyclic Carbenes[+]: Generation Under Mild Conditions and Formation of Group 8–10 Transition Metal Complexes Relevant to Catalysis", Chem. Eur. J. 1996, vol. 2, No. 7, ppg. 772–780.
Herrmann et al., "N–Heterocyclic Carbenes", Angew. Chem. Int. Ed. Engl., 1997, vol. 36, ppg. 2162–2187.
Huang, Jinkun et al., "Olefin Metahesis–Active Ruthenium Complexes Bearing a Nucleophilic Carbene Ligand", J. Am. Chem. Soc., 1999, vol. 121, No. 12, ppg. 2674–2678.

Huang et al., "Efficient Cross–Coupling of Aryl Chlorides With Aryl Grignard Reagents (Kumada Reactiion) Mediated by a Palladium/Imidazolium Chloride System", J. Am. Chem. Soc., 1999, vol. 121, No. 42, ppg. 9889–9890.
McGuinness, et al., "Synthesis and Reaction Chemistry of Mixed Ligand Methylpalladium–Carbene Complexes", J. Organometallic Chem., 1998, vol. 565, ppg. 165–178.
Alder, et al., "Stable Carbenes as Strong Bases", J. Chem. Soc., Chem. Commun, 1995, ppg. 1267–1268.
Arduengo, III et al., "A Stable Crystalline Carbene", J. Am. Chem. Soc., 1991, vol. 113, No. 1, ppg. 361–363.
Arduengo, III et al., "An Air Stable Carbene and Mixed Carbene "Dimers"", J. Am. Chem. Soc., 1997, vol. 119, No. 52, ppg. 12742–12749.
Schönherr, et al., "1.3.4.5–Tetraphenyl–imidazoliumperchlorat", Liebigs Ann. Chem. Bd. 731, 1970, ppg. 176–179 (not translated).
Chemical Abstracts, vol. 55, col. 21100, Wanzlick et al., "New Contribution to Carbene Chemistry", Angew Chem. vol. 72, p. 494, 1960.
Brescia et al., "Stereoselective Phenylation of Allylic Alcohol Derivatives by Palladium–Catalyzed Cross–Coupling with Hypervalent Silicon Complexes", J. Org. Chem., vol. 63, No. 10, 1998, ppg 3156–3157.

(List continued on next page.)

*Primary Examiner*—Floyd Higel
*Assistant Examiner*—Ebenezer Sackey
(74) *Attorney, Agent, or Firm*—Sieberth & Patty, L.L.C.

(57) ABSTRACT

This invention provides a process for conducting Kumada coupling reactions. The processes of the present invention make use of N-heterocyclic carbenes as ancillary ligands in Kumada couplings of aryl halides. A Kumada coupling can be carried out by mixing, in a liquid medium, at least one aryl halide, wherein the aryl halide has, directly bonded to the aromatic ring(s), at least one halogen atom selected from the group consisting of a chlorine atom, a bromine atom, and an iodine atom; at least one Grignard reagent; at least one metal compound comprising at least one metal atom selected from nickel, palladium, and platinum, wherein the formal oxidation state of the metal is zero or two; and at least one N-heterocyclic carbene. One preferred type of N-heterocyclic carbene is an imidazoline-2-ylidene of the formula

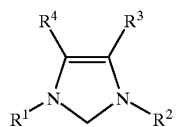

wherein $R^1$ and $R^2$ are each, independently, alkyl or aryl groups having at least 3 carbon atoms, $R^3$ and $R^4$ are each, independently, a hydrogen atom, a halogen atom, or a hydrocarbyl group. Homocoupling of aryl pseudohalides is also feasible using the processes of this invention.

75 Claims, No Drawings

OTHER PUBLICATIONS

Chuit et al., "Reactivity of Penta—and Hexacoordinate Silicon Compounds and Their Role as Reaction Intermediates", Chem. Rev., vol. 93, 1993, ppg 1371–1372 and 1440–1448.

Denmark et al., "Highly Stereospecific, Cross–Coupling Reactions of Alkenylsilacyclobutanes", J. Am. Chem. Soc., vol. 121, No. 24, 1999, ppg 5821–5822.

Denmark, et al., "Synthesis of Unsymmetrical Biaryls from Arylsilacyclobutanes", Organic Letters, vol. 1, No. 9, 1999, ppg 1495–1498.

Diederich et al., editors, Metal–catalyzed Cross–coupling Reactions, Wiley–VCH Publishing, Chapter 10, author Hiyama "Organosilicon Compounds in Cross–coupling Reactions", 1998, ppg 421–453.

"Group Notation Revised in Periodic Table" Chemical & Engineering News, 1985, vol. 63, ppgs. 26–27.

Hermann et al., "Chelating N–heterocyclic Carbene Ligands in Palladium–Catalyzed Heck–Type Reactions", Journal of Organometallic Chem., 1998, vol. 557, ppg. 93–96.

Hiyama et al., "Palladium–catalyzed cross–coupling reaction of organometalloids through activation with fluoride ion", Pure and Applied Chem., vol. 66, No. 7, 1994, ppg 1471–1478.

Horn, Keith, "Regio—and Stereochemical Aspects of the Palladium–Catalyzed Reactions of Silanes", Chem. Rev., vol. 95, 1995, ppg 1317–1350.

Huang, et al., "General and Efficient Catalytic Amination of Aryl Chlorides Using a Palladium/Bulky Nucleophilic Carbene System", Org. Lett. 1999, vol. 1, No. 8, ppg. 1307–1309.

Littke et al., "A convenient and general method for Pd–Catalyzed Suzuki Cross–Couplings or aryl Chlorides and Arylboronic Acids", Angew. Chem. Int. Ed. 1998, vol. 37, No. 24, ppg. 3387–3388.

Mowery et al., "Improvements in Cross Coupling Reactions of Hypervalent Siloxane Derivatives", Organic Letters, vol. 1, No. 13, 1999, ppg 2137–2140.

Mowery et al., "Cross–Coupling Reactions of Hypervalent Siloxane Derivatives: An Alternative to Stille and Suzuki Couplings", J. Org. Chem., vol. 64, No. 5, 1999, ppg 1684–1688.

Mowery et al., "Synthesis of Unsymmetrical Biaryls by Palladium–Catalzyed Cross Coupling Reactions of Arenes with Tetrabutylammonium Triphenyldifluorosilicate, a Hypervalent Silicon Reagent", J. Org. Chem., vol. 64, No. 9, 1999, ppg 3266–3270.

Old, et al., "A Highly Active Catalyst for Palladium–Catalyzed Cross–Coupling Reactions: Room–Temperature Suzuki Couplings and Amination of Unactivated Aryl Chlorides", J. Am. Chem. Soc., 1998, vol. 120, No. 37, ppgs. 9722–9723.

Pilcher et al., "Utilization of Tetrabutylammonium Triphenyldifluorosilicate as a Flouride Source for Silicon–Carbon Bond Cleavage", J. Org. Chem., vol. 61, No. 20, 1996, ppg 6901–6905.

Regitz, Manfred, "Nucleophilic Carbenes: An Incredible Renaissance", Angew. Chem. Int. Ed. Engl., 1996, vol. 35, No. 7, ppg. 725–728.

Wanzlick et al., "Direct Synthesis of a Mercury Salt–Carbene Complex", Angew Chem. Internat. Edit., 1968, vol. 7, No. 2, ppg. 141–142 and 154.

Wolfe, et al., "A Highly Active Catalyst for the Room–Temperature Amination and Suzuki Coupling of Aryl Chlorides", Angew. Chem. Int. Ed., 1999, vol. 38, No. 16, ppg. 2413–2416.

Zhang et al., "Palladium–Imidazol–2–Ylidene Complexes as Catalysts for Facile and Efficient Suzuki Cross–Coupling Reactions of Aryl Chlorides with Arylboronic Acids", J. Org. Chem., 1999, vol. 64, No. 11, ppg. 3804–3805.

USE OF A CATALYST SYSTEM COMPRISING NICKEL, PALLADIUM, OR PLATINUM AND IMIDAZOLINE-2-YLIDENE OR IMIDAZOLIDINE-2-YLIDENE IN KUMADA COUPLING REACTIONS

REFERENCE TO RELATED APPLICATIONS

This Application claims the priority date of U.S. Provisional Application No. 60/154,260 filed Sep. 22, 1999. U.S. Provisional Application No. 60/154,260 incorporates by reference U.S. Provisional Application No. 60/099,722, filed Sep. 10, 1998, and U.S. Provisional Application No. 60/121,056, filed Feb. 22, 1999.

Copending Application No. 09/507,959, filed Feb. 22, 2000, by us; copending Application No. 09/511,420, filed Feb. 22, 2000, by us; copending Application No. 09/507,958, filed Feb. 22, 2000, by us; and copending Application No. 09/511,654, filed Feb. 22, 2000, by us; may possibly be considered related to the present application.

This invention was made with Government support by the National Institute on Drug Abuse/National Science Foundation under Contract No. RO1 DA11528/9631611. The Government has certain rights in this invention.

TECHNICAL FIELD

This invention relates to Kumada coupling reactions, which can be used for chemical synthesis in the polymer and the fine chemical industry.

BACKGROUND

Metal catalyzed coupling reactions of aryl bromides, aryl iodides, and aryl pseudohalides (e.g., triflates) with various substrates is a general method employed for the formation of C—C bonds. Prior art methods generally cannot employ aryl chlorides as feedstock for these chemical transformations, and require the use of more expensive aryl bromides and aryl iodides. The use of aryl chlorides as chemical feedstock in coupling chemistry has proven difficult but would economically benefit a number of industrial processes. The few prior art methods that can employ aryl chlorides use expensive, air-sensitive phosphine ligands. In addition, phosphine ligands are often difficult to remove from the process product.

Nucleophilic N-heterocyclic carbenes, the imidazoline-2-ylidenes (sometimes commonly called imidazol-2-ylidenes) or so-called "phosphine mimics", have attracted considerable attention as possible alternatives for the widely used phosphine ligands in homogeneous catalysis. A primary advantage of these ligands is that an excess of the ligand is not required. It appears that these ligands do not dissociate from the metal center, thus preventing aggregation of the catalyst to yield the bulk metal.

THE INVENTION

This invention provides a process for conducting Kumada coupling reactions. The catalyst system used in the present invention permits the use of aryl chlorides as substrates in Kumada coupling reactions while eliminating the need for phosphine ligands. Furthermore, both electron-donating and electron-withdrawing substituents on the aryl halide or pseudohalide, the Grignard reagent, or both, in the Kumada coupling reaction are tolerated by the catalyst system used in the present invention, and provide the corresponding Kumada coupling products in excellent yields. Homocoupling of aryl pseudohalides is also feasible using the processes of this invention.

An embodiment of this invention provides a process which comprises mixing, in a liquid medium, i) at least one aryl halide wherein the aryl halide has, directly bonded to the aromatic ring(s), at least one halogen atom selected from the group consisting of a chlorine atom, a bromine atom, and an iodine atom; ii) at least one Grignard reagent; iii) at least one metal compound comprising at least one metal atom selected from nickel, palladium, and platinum, wherein the formal oxidation state of the metal is zero or two; and iv) at least one N-heterocyclic carbene. The N-heterocyclic carbene is selected from the group consisting of an imidazoline-2-ylidene wherein the 1 and 3 positions are each, independently, substituted by a secondary or tertiary group which has at least three atoms, or a protonated salt thereof; an imidazolidine-2-ylidene wherein the 1 and 3 positions are each, independently, substituted by a secondary or tertiary group which hag at least three atoms, or a protonated salt thereof; a bis(imidazoline-2-ylidene) wherein abridging moiety is bound to one nitrogen atom of each ring, and wherein the remaining two nitrogen atoms are each, independently, substituted by a secondary or tertiary group which has at least three atoms, or a protonated salt thereof; and a bis(imidazolidine-2-ylidene) wherein a bridging moiety is bound to one nitrogen atom of each ring, and wherein the remaining two nitrogen atoms are each, independently, substituted by a secondary or tertiary group which has at least three atoms, or a protonated salt thereof, or mixtures of two or more of the foregoing.

Another embodiment of this invention provides a process for homocoupling. This process comprises mixing, in a liquid medium, i) at least one aryl pseudohalide; ii) at least one metal compound comprising at least one metal atom selected from nickel, palladium, and platinum, wherein the formal oxidation state of the metal is zero or two; and iii) at least one N-heterocyclic carbene selected from the group described in the first embodiment.

Further embodiments and features of this invention will be apparent from the ensuing description and appended claims.

As noted above, there are two fundamental aspects to this invention. One aspect is the provision of exceedingly efficient catalyzed Kumada coupling reactions. The other aspect involves the discovery of catalyzed homocoupling reactions in which aryl triflates or aryl tosylates are caused to homocouple even in the presence of a Grignard reagent.

The liquid medium for the processes of this invention can include any of a wide range of solvents, and mixtures of solvents are also usable. The exclusion of water is necessary because the processes of this invention use Grignard reagents. Types of solvents that can be used include hydrocarbons, ethers, and amides. Polar solvents are preferred. When a hydrocarbon solvent is included in the liquid medium, it is preferred that the hydrocarbon solvent is makes up less than a third (by volume) of the liquid medium. Ethers are a preferred solvent type. Ethers that may be used include, for example, diethyl ether, di-n-propyl ether, diisopropyl ether, tert-butyl ethyl ether, diheptyl ether, 1,3-dioxolane, 1,4-dioxane, tetrahydrofuran, methyl tetrahydrofuran, glyme (the dimethyl ether of ethylene glycol), diglyme (the dimethyl ether of diethylene glycol), and the like. Cyclic ethers and polyethers are preferred, especially 1,4-dioxane and tetrahydrofuran. Mixtures comprising tetrahydrofuran are more preferred; a highly preferred liquid medium is a mixture of 1,4-dioxane and tetrahydrofuran.

Directly bonded to the aromatic ring(s) of the aryl halide or pseudohalide (i.e., aryl halide or aryl pseudohalide) is at least one halogen atom selected from a chlorine atom, a bromine atom, and an iodine atom, or at least one pseudohalide group. The term "pseudohalide group" includes such groups as p-toluene sulfonate (tosylate), trifluoromethanesulfonate (triflate), methanesulfonate (mesylate), nonaflate ($ON_f$) and aryl diazonium salts ($ArN_2^+X^\ominus$, where $X^\ominus$ is halide, $BF_4^\ominus$, etc.). The aryl halide or pseudohalide can have two or more such halogen atoms with an atomic number greater than nine and/or pseudohalide groups, including combinations of halogen atoms and pseudohalide groups. However, when two or more such groups are present, the halogen atoms with an atomic number greater than nine and/or pseudohalide groups should all be different from each other. For example, when two such substituents are present, they may be a chlorine atom and a bromine atom, or an iodine atom and a tosylate group, or etc. It is preferred that there is only one chlorine atom, bromine atom, iodine atom, or pseudohalide group directly bound to the aryl ring of the aryl halide or pseudohalide. Aryl chlorides are more preferred as the aryl halide reactants.

The aryl moiety for the aryl halide or pseudohalide can be homocyclic or heterocyclic. Examples of suitable homocyclic aryl moieties include, but are not limited to, benzene, naphthalene, anthracene, phenanthrene, pyrene, biphenyl, acenaphthalene, fluorene, and indene. Heterocyclic aryl moieties that can be used include, for example, furan, thiophene, pyridine, indole, oxathiolane, isoxazole, thianthrene, isobenzofuran, phenoxathin, and the like. Benzene is a preferred aryl moiety for the aryl halide or pseudohalide.

For the aryl halide or pseudohalide, substituents other than a chlorine atom, a bromine atom, an iodine atom, and/or a pseudohalide group that may be present on the aromatic ring(s) include, but are not limited to, hydrogen atoms, fluorine atoms, nitro groups, hydrocarbyl groups, alkoxy groups, perfluorohydrocarbyl groups, silyl groups, amino groups, ether groups, ketone groups, and ester groups. When hydrocarbyl groups are present, they are preferably $C_1$ to $C_{18}$ alkyl groups or $C_6$ to $C_{20}$ aryl or aralkyl groups. Examples of suitable hydrocarbyl groups are methyl, ethyl, isopropyl, tert-butyl, cyclopentyl, methylcyclohexyl, decyl, phenyl, tolyl, xylyl, benzyl, naphthyl, and tetrahydronaphthyl. Alkoxy group substituents preferably have $C_1$ to $C_6$ alkyl moieties. Some examples of alkoxy groups are methoxy, ethoxy, isopropoxy, methylcyclopentoxy, and cyclohexoxy. Perfluorohydrocarbyl groups include alkyl and aryl perfluorocarbons; suitable perfluorohydrocarbyl groups are, for example, trifluoromethyl, pentafluoroethyl, pentafluorophenyl, and heptafluoronaphthyl. Substituent silyl groups preferably have $C_1$ to $C_{18}$ alkyl groups or $C_6$ to $C_{20}$ aryl or aralkyl groups, and examples include trimethylsilyl, triisopropylsilyl, tert-butyl(dimethyl)silyl, tridecylsilyl, and triphenylsilyl. The substituents preferred for the aryl halide or pseudohalide will depend on the product that is desired.

The Grignard reagent can be an organomagnesium chloride, an organomagnesium bromide, or an organomagnesium iodide, and is preferably an organomagnesium bromide. The organic group of the Grignard reagent may be saturated, unsaturated, branched, straight-chain, cyclic, or aromatic. Heteroatoms, such as oxygen, sulfur, and silicon can be present in the organic group of the Grignard reagent. The organic group of the Grignard reagent is preferably an aromatic group. The aryl moiety of the aromatic group can be homocyclic or heterocyclic, as described for the aryl halide or pseudohalide. For the Grignard reagent, the preferred aryl moieties are benzene and naphthalene. Substituents on the aryl ring, as described for the aryl halide or pseudohalide, can be hydrogen atoms, fluorine atoms, nitro groups, hydrocarbyl groups, alkoxy groups, perfluorohydrocarbyl groups, and silyl groups. Preferred substituents for the Grignard reagent depend on the desired product.

The metal compound comprises at least one metal atom selected from nickel, palladium, and platinum having a formal oxidation state of zero or two, and is sometimes referred to hereinafter as the metal compound. Inorganic salts of nickel, palladium, or platinum that can be used include the bromides, chlorides, fluorides, iodides, cyanides, nitrates, sulfides, sulfites, and sulfates. Organic nickel, palladium, or platinum compounds that may be used include complexes and salts such as the carboxylates, e.g., the acetates or propionates, etc. Suitable nickel compounds include bis(1,5-cyclooctadiene)nickel, nickel acetate, nickel oxalate, nickel phosphate, nickel stearate, nickel acetylacetonate, nickel tetrafluoroborate, nickel thiocyanate, nickel carbonate, and nickel sulfamate. Examples of palladium compounds include $Pd(OAc)_2$, palladium(II) chloride, $Pd(CH_3CN)_4(BF_4)_2$, $PdCl_2(CH_3CN)_2$, $PdCl_2(PhCN)_2$, $PdCl_2(PPh_3)_2$, tris(dibenzylideneacetone)dipalladium(0) [which is also referred to herein as dipalladium tris (dibenzylideneacetone)], and palladium trifluoroacetate. Platinum compounds that can be used include platinum acetylacetonate and platinum chloride. Nickel and palladium compounds are preferred; more preferred are compounds of palladium. Palladium compounds such as palladium acetate and tris(dibenzylideneacetone)dipalladium(0) are most preferred.

Preferred types of N-heterocyclic carbenes are imidazoline-2-ylidenes of the formula

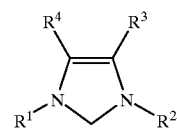

or protonated salts thereof, wherein $R^1$ and $R^2$ are each, independently, alkyl or aryl groups having at least 3 carbon atoms, $R^3$ and $R^4$ are each, independently, a hydrogen atom, a halogen atom, or a hydrocarbyl group;

imidazolidine-2-ylidenes of the formula

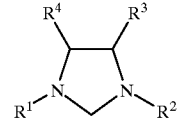

or protonated salts thereof, wherein $R^1$, $R^2$, $R^3$, and $R^4$ are as defined for the imidazoline-2-ylidenes;

bis(imidazoline-2-ylidene)s of the formula

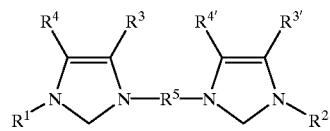

or protonated salts thereof, wherein $R^1$, $R^2$, $R^3$, and $R^4$ are as defined for the imidazoline-2-ylidenes, wherein $R^{3'}$ and $R^{4'}$ are as defined for $R^3$ and $R^4$ for the imidazoline- 2-ylidenes, and wherein $R^5$ is a bridging group that links the two imidazoline rings;

bis(imidazolidine-2-ylidene)s of the formula

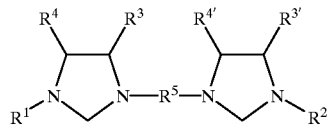

or protonated salts thereof, wherein $R^1$, $R^2$, $R^3$, and $R^4$ are as defined for the imidazoline-2-ylidenes, wherein $R^{3'}$ and $R^{4'}$ are as defined for $R^3$ and $R^4$ for the imidazoline-2-ylidenes, and wherein $R^5$ is a bridging group that links the two imidazolidine rings.

$R^1$ and $R^2$ are preferably sterically bulky groups. Suitable groups include, but are not limited to, isopropyl, sec-butyl, tert-butyl, 2,2-dimethylpropyl (neopentyl), cyclohexyl, norbornyl, adamantyl, tolyl, 3,5-dimethylphenyl, 2,4,6-trimethylphenyl, 2,6-diisopropylphenyl, and triphenylmethyl. Preferred groups are tert-butyl, 2,4,6-trimethylphenyl, 2,6-diisopropylphenyl, 2,4,6-triisopropylphenyl, 2,4,6-triisopropylphenylmethyl and triphenylmethyl. Most preferred for both $R^1$ and $R^2$ are the 2,4,6-trimethylphenyl and 2,6-diisopropylphenyl groups.

Examples of suitable $R^3$, $R^4$, $R^{3'}$, and $R^{4'}$ groups include chlorine atoms, bromine atoms, hydrogen atoms, hydrocarbyl groups, and the like. When hydrocarbyl groups are present, they are preferably $C_1$ to $C_{18}$ alkyl groups or $C_6$ to $C_{20}$ aryl or aralkyl groups. Examples of suitable hydrocarbyl groups are methyl, ethyl, isopropyl, tert-butyl, cyclopentyl, methylcyclohexyl, decyl, phenyl, tolyl, xylyl, benzyl, naphthyl, and tetrahydronaphthyl. Chlorine atoms and hydrogen atoms are preferred groups. Most preferred for all substituents $R^3$, $R^4$, $R^{3'}$, and $R^{4'}$ are hydrogen atoms.

$R^5$ in both the formula for the bis(imidazoline-2-ylidene)s and the bis(imidazolidine-2-ylidene)s of this invention can be selected from a large variety of moieties, including alkylene groups, arylene groups, and silylene groups. Atoms that can form the bridge include, but are not limited to, carbon, nitrogen, oxygen, silicon, and sulfur. Examples of suitable bridging moieties include methylene (—CH$_2$—), substituted methylene, ethylene (—CH$_2$CH$_2$—), substituted ethylene, silylene (>SiR$_2$), benzo (C$_6$H$_4$<), substituted benzo, biphenylene, substituted biphenylene, binaphthylene, and substituted binaphthylene. Heterocyclic aromatic moieties such as, for example, pyridine, pyrimidine, pyridine, pyridazine, furan, thiophene, oxathiolane, thianthrene, isobenzofuran, phenoxathin, isothiazole, phenoxazine, and the like, can also form the bridge. Preferred $R^5$ moieties include biphenylene, binaphthylene, and substituted benzo, with substituted benzo being more preferred. Highly preferred is benzo substituted with methyl groups. The bridge has at least one atom, and preferably has from four to eight atoms. While better results have been observed with longer bridges, it is possible that judicious choices for $R^1$, $R^2$, $R^3$, $R^4$, $R^{3'}$, and $R^{4'}$ may improve results for short bridges.

Without being bound by theory, it appears from thermochemical studies that the electron-donating ability of many of the imidazoline-2-ylidene carbene ligands is better than that of tri(cyclohexyl)phosphine and the steric demand of these carbene ligands is greater than that of tri(cyclohexyl)phosphine. This suggests that the N-heterocyclic carbene should possess steric bulk sufficient to stabilize both the free-carbene and to stabilize reaction intermediates. However, imidazoline-2-ylidene carbenes and imidazolidine-2-ylidene carbenes are considerably less stable to air and moisture than their corresponding protonated imidazolinium and imidazolinium salts. Thus, a highly preferred embodiment of this invention involves generation of the imidazoline-2-ylidene in situ from the corresponding imidazolinium salt (similarly so for the imidazolidine-2-ylidene and the corresponding imidazolinium salt); this removes the need to handle the N-heterocyclic carbene ligands in an inert atmosphere. Protonated salts of the imidazoline-2-ylidene carbenes and imidazolidine-2-ylidene carbenes are monoprotonated, while the protonated salts of the bis(imidazoline-2-ylidene)s and the bis(imidazolidine-2-ylidene)s are diprotonated. Suitable counterions for the protonated salts are virtually limitless, but halides are preferred counterions. The most preferred counterions are chloride and bromide. The imidazolinium salts are straightforward to synthesize and are air-stable. While the absence of oxygen is not necessary when using a protonated salt of an imidazoline-2-ylidene carbene or an imidazolidine-2-ylidene carbene, it is preferred. When using a neutral carbene, the absence of oxygen is necessary. In any instance where oxygen is excluded, the presence of an inert gas such as nitrogen, helium, or argon is preferred.

For the Kumada coupling reaction, the aryl halide or pseudohalide and the Grignard reagent may be employed in an ideal molar ratio of about 1:1 when using an aryl halide or pseudohalide that has only one halogen atom (other than a fluorine atom) or pseudohalide group; or either reagent may be used in excess. It is preferred to use the Grignard reagent in an excess such that the molar ratio of aryl halide or pseudohalide to Grignard reagent is in the range of from about 1:1 to about 1:5 when using an aryl halide or pseudohalide that has only one halogen atom (other than a fluorine atom) or pseudohalide group. When the aryl halide or pseudohalide has more than one halogen atom (other than fluorine) and/or pseudohalide group, reactions may be carried out in sequence. A Grignard reagent will react first at the site of the more reactive substituent, e.g., at iodine before bromine. Reaction at only the site of the more reactive substituent(s) can be performed. In reactions carried out in sequence where the Grignard reagents are different, each should be added separately. It is preferred to allow one reaction to finish before the addition of the next Grignard reagent. When different Grignard reagents are used, it is preferred to use close to the ideal molar ratio of aryl halide or pseudohalide to Grignard reagent to minimize undesirable side products. The presence of a Grignard reagent is not necessary in a homocoupling reaction.

Normally, the molar ratio of metal atoms of the metal compound to aryl halide or pseudohalide molecules is in the range of from about 0.01:1 to about 0.05:1; a preferred molar ratio of metal atoms of metal compound to aryl halide or pseudohalide molecules is in the range of from about 0.02:1 to about 0.04:1. For the metal compound and the carbene ligands, the molar ratio of metal atoms of the metal compound to carbene molecules is in the range of from about 1:0.5 to about 1:5, and more preferably in the range of from about 1:0.5 to about 1:2.5.

The order of addition of the various components to a reaction vessel is not of particular importance for either heterocoupling or homocoupling reactions. Premixing of the components of the catalyst system is not necessary; however, it is preferred for both heterocoupling and homocoupling reactions that the catalyst system is premixed. To premix the components of the catalyst system, the metal compound and the N-heterocyclic carbene (salt or neutral compound), are mixed together after being added in no particular order to a reaction vessel. The mixing time (activation period) for these components on the laboratory scale may be very short, e.g., five minutes or less, but a preferred mixing time is in the range of from about fifteen minutes to about sixty minutes.

If a premixed catalyst system is used, the aryl halide or pseudohalide and the Grignard reagent may be added to the same reaction vessel, or the premixed catalyst system can be transferred to a different vessel in which the reaction is to take place. Use of the same vessel for premixing the catalyst system and conducting the reaction is preferred.

For both heterocoupling and homocoupling reactions, when the components of the catalyst system are not premixed, all of the components of the reaction mixture are added in any order to the reaction vessel.

Once all of the components are present in the same reaction vessel, the mixture may be heated, provided that the temperature does not exceed the thermal decomposition temperature of the catalyst system or the products of the reaction. Preferred temperatures for both heterocoupling and homocoupling reactions are in the range of from about 20° C. to about 150° C.; more preferred temperatures are in the range of from about 20° C. to about 120° C. When the aryl halide is an aryl chloride, or when the aryl pseudohalide is an aryl triflate or an aryl tosylate, heat is usually necessary to drive the reaction. Preferred temperatures when the aryl halide is an aryl chloride, or when the aryl pseudohalide is an aryl triflate or an aryl tosylate are in the range of from about 40° C. to about 150° C. When the aryl halide is an aryl bromide or an aryl iodide, the reaction(s) proceeds easily at room temperature, although heat may speed the reaction. For aryl bromides and aryl iodides, preferred temperatures are in the range of from about 20° C. to about 70° C.

When a Grignard reagent is used, the exclusion of water is generally required; thus, heterocoupling reactions are normally carried out in the absence of water. While not necessary when using protonated salts of N-heterocyclic carbenes, the absence of oxygen is to preferred when conducting the processes of this invention. Conversely, the exclusion of oxygen and water is generally necessary when neutral carbenes are used. The presence of an inert gas such as argon or nitrogen is preferred when oxygen and/or water are excluded. The reaction mixture is normally agitated. A preferred contact time for the components of either a heterocoupling or a homocoupling reaction is in the range of from about one hour to about seventy-two hours. More preferably, the contact time is from about one hour to about forty-eight hours.

The following examples are presented for purposes of illustration, and are not intended to impose limitations on the scope of this invention.

EXAMPLES

General Procedures

Reagents. All aryl halides (Aldrich Chemical Company), arylmagnesium bromides (1.0 moles per liter in tetrahydrofuran; Aldrich), 1,4-dioxane (anhydrous, Aldrich), and $Pd_2$(dibenzylideneacetone)$_3$ (Strem Chemical Company) were used as received. Flash chromatography was performed on silica gel 60 (230–400 mesh; Natland International Corporation).

1,3-Bis(substituted)imidazoline-2-ylidenes and 1,3-bis(substituted)imidazolinium chlorides were prepared according to reported procedures in U.S. Pat. No. 5,077,414, and/or Arduengo, A. J. III., Dias, H. V. R.; Harlow, R. L. and Kline, M. *J. Am. Chem. Soc.*, 1992, 114, 5530–5534. The synthesis of 1,3-bis(2,6-diisopropylphenyl)imidazolinium chloride was carried out in a similar fashion, except that it was done in two steps (rather than in one pot).

Analyses. All reactions were monitored by thin layer chromatography (TLC). $^1$H and $^{13}$C nuclear magnetic resonance (NMR) spectra were recorded on a 300 MHZ NMR spectrometer (Varian, Incorporated) or 400 MHZ NMR spectrometer (Varian) at ambient temperature in $CDCl_3$ (Cambridge Isotope Laboratories, Incorporated). All of the products had $^1$H NMR spectra identical with literature data.

Conditions. All reactions were carried out under an atmosphere of argon in oven-dried glassware with magnetic stirring, unless otherwise indicated.

Example 1

For each run, a Schlenk tube was charged with $Pd_2$(dibenzylideneacetone)$_3$ (10 mg, 0.01 mmol), 1,3-bis(substituted)imidazolinium chloride (0.04 mmol), and a magnetic stirring bar. After a 30 minute catalyst activation period, solvent (5 mL), 4-chlorotoluene (1.0 mmol), and phenylmagnesium bromide (1.2 mmol) were added in turn to the Schlenk tube. The Schlenk tube was placed in an oil bath and the mixture was heated and stirred for a number of hours. The mixture was then allowed to cool to room temperature. The mixture was hydrolyzed either with aqueous HCl (1.0 moles per liter) or $H_4NCl$ solution. The solvent was removed under vacuum and the residue was purified by flash chromatography using hexane or a mixture of hexane and ethyl acetate.

The 1,3-bis(substituted)imidazolinium chloride used in each run are listed in Table 1. All of the yields reported in Table 1 are of the heterocoupling product, and are the average of two runs.

TABLE 1

| Run | 1,3-bis(substituted) imidazolinium chloride | Solvent | T | Reaction time | Isolated yield |
|---|---|---|---|---|---|
| a | 1,3-Bis(2,4,6-trimethylphenyl) imidazolinium chloride | $Et_2O$/THF | 45° C. | 20 hr. | 35% |
| b | 1,3-Bis(2,6-diisopropylphenyl) imidazolinium chloride | $Et_2O$/THF | 45° C. | 20 hr. | 97% |
| c | 1,3-Bis(2,6-diisopropylphenyl) imidazolinium chloride | toluene/THF | 80° C. | 20 hr. | 10% |
| d | 1,3-Bis(2,6-diisopropylphenyl) imidazolinium chloride | THF | 80° C. | 5 hr. | 86% |
| e | None | dioxane/THF | 80° C. | 3 hr. | 0 |
| f | 1,3-Bis(2,4,6-trimethylphenyl) imidazolinium chloride | dioxane/THF | 80° C. | 3 hr. | 41% |
| g | 1,3-Bis(2,6-diisopropylphenyl) imidazolinium chloride | dioxane/THF | 80° C. | 3 hr. | 99% |

Example 2

Reagents, analyses, and procedures were as described in Example 1, except as follows. In all runs, the solvent was a mixture of 1,4-dioxane and tetrahydrofuran; the 1,3-bis(substituted)imidazolinium chloride used was 1,3-bis(2,6-diisopropylphenyl)imidazolinium chloride. All runs were performed at 80° C. Several different aryl halides (1.0 mmol each) and Grignard reagents (1.2 mmol each) were used. In Run B, $Pd(CH_3CO_2)_2$ (4.5 mg, 0.02 mmol) was used as the metal compound; in Run F, 1.8 mmol of the Grignard reagent was used, and in Runs H and I, 2.5 mmol of the Grignard reagent was used.

The aryl halides and Grignard reagents used in each run are listed in Table 2. All of the yields reported in Table 2 are of the heterocoupling product, and are the average of two runs.

TABLE 2

| Run | Aryl halide | Grignard reagent | Reaction time | Isolated yield |
|---|---|---|---|---|
| A | 4-Chorotoluene | Phenylmagnesium bromide | 3 hr. | 99% |
| B | 4-Chorotoluene | Phenylmagnesium bromide | 3 hr. | 96% |
| C | 4-Bromotoluene | Phenylmagnesium bromide | 1 hr. | 99% |
| D | 1-Methoxy-4-chlorobenzene | Phenylmagnesium bromide | 3 hr. | 97% |
| E | 1,4-Dimethyl-2-chlorobenzene | Phenylmagnesium bromide | 3 hr. | 85% |
| F | 1,3-Dimethyl-2-chlorobenzene | Phenylmagnesium bromide | 5 hr. | 87% |
| G | Methyl-4-bromobenzoate | Phenylmagnesium bromide | 5 hr. | 69% |
| H | 4-Iodophenol | Phenylmagnesium bromide | 3 hr. | 96% |
| I | 4-Chlorophenol | Phenylmagnesium bromide | 5 hr. | 95% |
| J | 6-Methoxy-2-bromonaphthalene | Phenylmagnesium bromide | 1 hr. | 98% |
| K | 1-Methoxy-4-chlorobenzene | 4-Methylphenylmagnesium bromide | 3 hr. | 99% |
| L | 1-Methoxy-4-chlorobenzene | 3-Methylphenylmagnesium bromide | 3 hr. | 83% |
| M | 1-Methoxy-4-chlorobenzene | 2-Fluorophenyl magnesium bromide | 3 hr. | 99% |
| N | 1-Methoxy-4-chlorobenzene | 2,4,6-Trimethylphenylmagnesium bromide bromide | 3 hr. | 95% |
| O | 1,3-Dimethyl-2-chlorobenzene | 2,4,6-Trimethylphenylmagnesium bromide bromide | 24 hr. | 0 |
| P | 1,3,5-Trimethyl-2-bromobenzene | 2,4,6-Trimethylphenylmagnesium bromide bromide | 24 hr. | 0 |

Example 3

Reagents, analyses, and procedures were as described in Example 1, except as follows. In all runs, the $Pd_2$(dibenzylideneacetone)$_3$ was used in the amount of 0.02 mmol; the solvent was 1,4-dioxane; the 1,3-bis(substituted) imidazolinium chloride used was 1,3-bis(2,6-diisopropylphenyl)imidazolinium chloride in the amount of 0.02 mmol. All runs were performed at 80° C. for 48 hours. Several different aryl chlorides (1.0 mmol each) and Grignard reagents (1.2 mmol each) were used.

The aryl chlorides and Grignard reagents used in each run are listed in Table 3. All of the yields reported in Table 3 are of the heterocoupling product, and are the average of two runs.

TABLE 3

| Run | Aryl halide | Grignard reagent | Isolated yield |
|---|---|---|---|
| a | 4-Chorotoluene | Vinylmagnesium bromide | 26% |
| b | 1-Methoxy-4-chlorobenzene | Vinylmagnesium bromide | 14% |
| c | Methyl-4-chlorobenzoate | Vinylmagnesium bromide | 10% |
| d | 4-Chorotoluene | n-Butylmagnesium bromide | 8% |
| e | 4-Chorotoluene | sec-Butylmagnesium bromide | 16% |

Example 4

Reagents, analyses, and procedures were as described in Example 1, except as follows. In all runs, the $Pd_2$(dibenzylideneacetone)$_3$ was used in the amount of 0.02 mmol; the solvent was 1,4-dioxane; the 1,3-bis(substituted) imidazolinium chloride used was 1,3-bis(2,6-diisopropylphenyl)imidazolinium chloride in the amount of 0.02 mmol. All runs were performed at 80° C. for 48 hours. Several different aryl tosylates (1.0 mmol each) and an aryl triflate (1.0 mmol) were used. Homocoupling products of the aryl triflates and the aryl tosylates were observed in all runs other than Run A.

The aryl pseudohalides used in each run are listed in Table 4. All reactions yielded the homocoupling product of the aryl pseudohalide.

TABLE 4

| Run | Aryl pseudohalide | Principal product |
|---|---|---|
| A | 4-Methylphenyl triflate | Homocoupling product of aryl triflate |
| B | 4-Methylphenyl triflate | Homocoupling product of aryl triflate |
| C | 4-Methoxyphenyl triflate | Homocoupling product of aryl triflate |
| D | 4-$CH_3CO_2$-phenyl triflate | Homocoupling product of aryl triflate |
| E | 4-Methylphenyl tosylate | Homocoupling product of aryl tosylate |

Example 4 demonstrates that the process of this invention is useful in the homocoupling of aryl triflates and aryl tosylates.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Whatever transformations, if any, that occur in situ as a reaction is conducted is what the claim is intended to cover. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for conducting a reaction in which a hetero-coupling reaction product is formed, which process comprises mixing, in a liquid medium, in the absence of water,
   i) at least one aryl halide wherein the aryl halide has, directly bonded to the aromatic ring(s), at least one halogen atom selected from the group consisting of a chlorine atom, a bromine atom, and an iodine atom;
   ii) at least one Grignard reagent;
   iii) at least one metal compound comprising at least one metal atom selected from nickel, palladium, and platinum, wherein the formal oxidation state of the metal is zero or two; and
   iv) at least one N-heterocyclic carbene selected from the group consisting of an imidazoline-2-ylidene wherein the 1 and 3 positions are each, independently, substituted by a secondary or tertiary group which has at least three atoms, or a protonated salt thereof; an imidazolidine-2-ylidene wherein the 1 and 3 positions are each, independently, substituted by a secondary or tertiary group which has at least three atoms, or a protonated salt thereof; a bis(imidazoline2-ylidene) wherein a bridging moiety is bound to one nitrogen atom of each ring, and wherein the remaining two nitrogen atoms are each, independently, substituted by a secondary or tertiary group which has at least three atoms, or a protonated salt thereof; and a bis(imidazolidine-2-ylidene) wherein a bridging moiety is bound to one nitrogen atom of each ring, and wherein the remaining two nitrogen atoms are each, independently, substituted by a secondary or tertiary group which has at least three atoms, or a protonated salt thereof, or mixtures of two or more of the foregoing.

2. A process according to claim 1 wherein said N-heterocyclic carbene is an imidazoline-2-ylidene of the formula

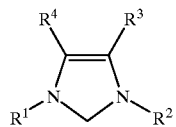

or a protonated salt thereof, wherein
$R^1$ and $R^2$ are each, independently, alkyl or aryl groups having at least 3 carbon atoms, and
$R^3$ and $R^4$ are each, independently, a hydrogen atom, a halogen atom, or a hydrocarbyl group.

3. A process according to claim 1 wherein said N-heterocyclic carbene is an imidazolidine-2-ylidene of the formula

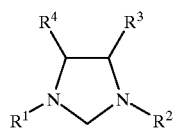

or a protonated salt thereof, wherein
$R^1$ and $R^2$ are each, independently, alkyl or aryl groups having at least 3 carbon atoms, and
$R^3$ and $R^4$ are each, independently, a hydrogen atom, a halogen atom, or a hydrocarbyl group.

4. A process according to claim 1 wherein said N-heterocyclic carbene is a bis(imidazoline-2-ylidene) of the formula

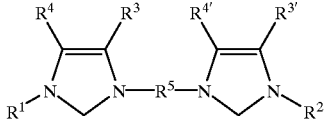

or a protonated salt thereof, wherein
$R^1$ and $R^2$ are each, independently, alkyl or aryl groups having at least 3 carbon atoms,
$R^3$ and $R^4$ are each, independently, a hydrogen atom, a halogen atom, or a hydrocarbyl group,
$R^{3'}$ and $R^{4'}$ are as defined for $R^3$ and $R^4$, and
$R^5$ is a bridging group that links the two imidazoline rings.

5. A process according to claim 1 wherein said N-heterocyclic carbene is a bis(imidazolidine-2-ylidene) of the formula

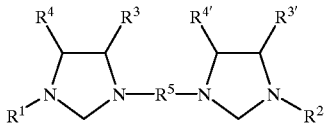

or a protonated salt thereof, wherein
$R^1$ and $R^2$ are each, independently, alkyl or aryl groups having at least 3 carbon atoms,
$R^3$ and $R^4$ are each, independently, a hydrogen atom, a halogen atom, or a hydrocarbyl group,
$R^{3'}$ and $R^{4'}$ are as defined for $R^3$ and $R^4$, and $R^5$ is a bridging group that links the two imidazoline rings.

6. A process according to claim 1 wherein said liquid medium comprises at least one ether.

7. A process according to claim 6 wherein said ether is a cyclic ether.

8. A process according to claim 7 wherein said ether is 1,4-dioxane.

9. A process according to claim 7 wherein said ether is tetrahydrofuran.

10. A process according to claim 6 wherein said liquid medium is a mixture of two or more ethers.

11. A process according to claim 1 wherein said aryl halide is an aryl chloride.

12. A process according to claim 11 wherein said aryl chloride is selected from the group consisting of 4-chlorotoluene, 1-methoxy-4-chlorobenzene, 1,4-dimethyl-2-chlorobenzene, and methyl-4-chlorobenzoate.

13. A process according to claim 1 wherein said aryl halide is an aryl bromide.

14. A process according to claim 13 wherein said aryl bromide is either 4-bromotoluene or methyl-4-bromobenzoate.

15. A process according to claim 1 wherein said aryl halide is a phenyl halide.

16. A process according to claim 15 wherein said phenyl halide is chlorobenzene.

17. A process according to claim 1 wherein said aryl halide is a naphthyl halide.

18. A process according to claim 17 wherein said naphthyl halide is either 1-bromonaphthalene or 6-methoxy-2-bromonaphthalene.

19. A process according to claim 1 wherein said Grignard reagent is a phenylmagnesium halide.

20. A process according to claim 19 wherein said phenylmagnesium halide is selected from the group consisting of 2-fluorophenylmagnesium bromide, 3-methylphenylmagnesium bromide, 4-methylphenylmagnesium bromide, 2,4,6-trimethylphenylmagnesium bromide, and phenylmagnesium bromide.

21. A process according to claim 1 wherein said Grignard reagent is a naphthylmagnesium halide.

22. A process according to claim 21 wherein said naphthylmagnesium halide is either 6-methoxy-2-naphthylmagnesium bromide or 1-naphthylmagnesium bromide.

23. A process according to claim 1 wherein said metal compound comprises a palladium compound.

24. A process according to claim 23 wherein said palladium compound is selected from the group consisting of palladium acetate, palladium chloride, and dipalladium tris (dibenzylideneacetone).

25. A process according to claim 1 wherein said metal compound comprises a nickel compound.

26. A process according to claim 25 wherein said nickel compound is bis(1,5-cyclooctadiene)nickel.

27. A process according to claim 1 wherein the metal compound is selected from the group consisting of palladium acetate, palladium chloride, and dipalladium tris (dibenzylideneacetone), and wherein the aryl halide is an aryl chloride.

28. A process according to claim 1 wherein said N-heterocyclic carbene is an imidazoline-2-ylidene or a protonated salt thereof.

29. A process according to claim 2 wherein $R^1$ and $R^2$ of said N-heterocyclic carbene are the same, and each is a 2,4,6-trimethylphenyl group or a 2,6-diisopropylphenyl group.

30. A process according to claim 3 wherein $R^1$ and $R^2$ of said N-heterocyclic carbene are the same, and each is a 2,4,6-trimethylphenyl group or a 2,6-diisopropylphenyl group.

31. A process according to claim 4 wherein $R^1$ and $R^2$ of said N-heterocyclic carbene are the same, and each is a 2,4,6-trimethylphenyl group or a 2,6-diisopropylphenyl group.

32. A process according to claim 5 wherein $R^1$ and $R^2$ of said N-heterocyclic carbene are the same, and each is a 2,4,6-trimethylphenyl group or a 2,6-diisopropylphenyl group.

33. A process according to claim 30 wherein said N-heterocyclic carbene is a protonated salt of an imidazoline-2-ylidene.

34. A process according to claim 2 wherein $R^3$ and $R^4$ of said N-heterocyclic carbene are the same, and each is a hydrogen atom.

35. A process according to claim 3 wherein $R^3$ and $R^4$ of said N-heterocyclic carbene are the same, and each is a hydrogen atom.

36. A process according to claim 4 wherein $R^3$ and $R^4$ of said N-heterocyclic carbene are the same, and each is a hydrogen atom.

37. A process according to claim 5 wherein $R^3$ and $R^4$ of said N-heterocyclic carbene are the same, and each is a hydrogen atom.

38. A process according to claim 29 wherein $R^3$ and $R^4$ of said N-heterocyclic carbene are the same, and each is a hydrogen atom.

39. A process according to claim 29 wherein said metal compound is a palladium compound.

40. A process according to claim 39 wherein said palladium compound is selected from the group consisting of palladium acetate, palladium chloride, and dipalladium tris (dibenzylideneacetone).

41. A process according to claim 29 wherein the molar ratio of metal atoms of the metal compound to aryl halide molecules is in the range of from about 0.01:1 to about 0.05:1.

42. A process according to claim 4 wherein said N-heterocyclic carbene is a protonated salt of a bis (imidazoline-2-ylidene).

43. A process according to claim 42 wherein $R^1$ and $R^2$ of said protonated salt are the same, and each is selected from the group consisting of a 2,4,6-trimethylphenyl group, a 2,6-diisopropylphenyl group and a 2,4,6-triisopropylphenyl group.

44. A process according to claim 42 wherein $R^{3'}$ and $R^{4'}$ of said protonated salt are the same, and each is a hydrogen atom.

45. A process according to claim 4 wherein $R^{3'}$ and $R^{4'}$ of said N-heterocyclic carbene are the same, and each is a hydrogen atom.

46. A process according to claim 5 wherein $R^{3'}$ and $R^{4'}$ of said N-heterocyclic carbene are the same, and each is a hydrogen atom.

47. A process according to claim 42 wherein $R^3$ and $R^4$ of said protonated salt are the same, and each is a hydrogen atom.

48. A process according to claim 43 wherein said metal compound is a palladium compound.

49. A process according to claim 48 wherein said palladium compound is palladium acetate.

50. A process according to claim 43 wherein the molar ratio of metal atoms of the metal compound to aryl halide molecules is in the range of from about 0.01:1 to about 0.05:1.

51. A process according to claim 43 wherein said protonated salt of the bis(imidazoline-2-ylidene) is either

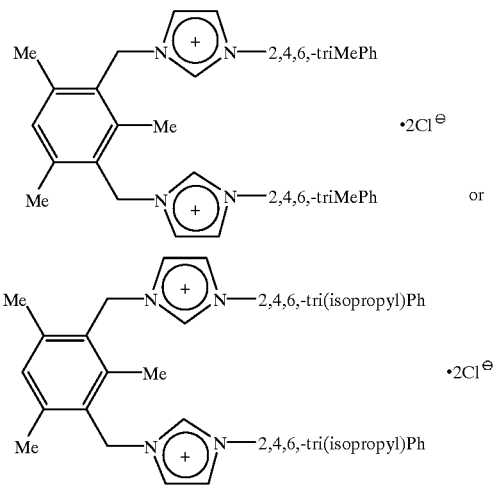

52. A process according to claim 4 wherein the bridge formed by $R^5$ has at least four atoms.

53. A process according to claim 52 wherein the bridge formed by $R^5$ has four to eight atoms.

54. A process according to claim 5 wherein the bridge formed by $R^5$ has four to eight atoms.

55. A process according to claim 4 wherein $R^5$ is a substituted benzo moiety.

56. A process according to claim 5 wherein $R^5$ is a substituted benzo moiety.

57. A process according to claim 1 wherein the molar ratio of aryl halide to Grignard reagent is in the range of from about 1:1 to about 1:5.

58. A process according to claim 1 wherein the molar ratio of metal atoms of the metal compound to aryl halide molecules is in the range of from about 0.01:1 to about 0.05:1.

59. A process according to claim 1 wherein the molar ratio of metal atoms of the metal compound to N-heterocyclic carbene is in the range of from about 1:0.5 to about 1:5.

60. A process according to claim 1 wherein the temperature is in the range of from about 20° C. to about 150° C.

61. A process according to claim 1 wherein said aryl halide is an aryl chloride, and wherein the temperature is in the range of from about 40° C. to about 150° C.

62. A process according to claim 1 wherein said aryl halide is either an aryl bromide or an aryl iodide, and wherein the temperature is in the range of from about 20° C. to about 70° C.

63. A process for conducting a reaction in which a product of homocoupling of aryl pseudohalides is formed, which process comprises mixing, in a liquid medium
   i) at least one aryl pseudohalide;
   ii) at least one metal compound comprising at least one metal atom selected from nickel, palladium, and platinum, wherein the formal oxidation state of the metal is zero or two; and
   iii) at least one N-heterocyclic carbene selected from the group consisting of an imidazoline-2-ylidene wherein the 1 and 3 positions are each, independently, substituted by a secondary or tertiary group which has at least three atoms, or a protonated salt thereof; an imidazolidine-2-ylidene wherein the 1 and 3 positions are each, independently, substituted by a secondary or tertiary group which has at least three atoms, or a protonated salt thereof; a bis(imidazoline-2-ylidene) wherein a bridging moiety is bound to one nitrogen atom of each ring, and wherein the remaining two nitrogen atoms are each, independently, substituted by a secondary or tertiary group which has at least three atoms, or a protonated salt thereof; and a bis(imidazolidine-2-ylidene) wherein a bridging moiety is bound to one nitrogen atom of each ring, and wherein the remaining two nitrogen atoms are each, independently, substituted by a secondary or tertiary group which has at least three atoms, or a protonated salt thereof, or mixtures of two or more of the foregoing.

64. A process according to claim 63 wherein said N-heterocyclic carbene is an imidazoline-2-ylidene of the formula

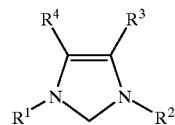

or a protonated salt thereof, wherein $R^1$ and $R^2$ are each, independently, alkyl or aryl groups having at least 3 carbon atoms, and $R^3$ and $^4$ are each, independently, a hydrogen atom, a halogen atom, or a hydrocarbyl group.

65. A process according to claim 63 wherein said liquid medium comprises at least one ether.

66. A process according to claim 65 wherein said ether is 1,4-dioxane.

67. A process according to claim 63 wherein said aryl pseudohalide is an aryl trifluoromethanesulfonate.

68. A process according to claim 63 wherein said aryl pseudohalide is an aryl toluene sulfonate.

69. A process according to claim 63 wherein said aryl pseudohalide is selected from the group consisting of 4-methylphenyl trifluoromethanesulfonate, 4-methoxyphenyl trifluoromethanesulfonate, and 4-methoxyphenyl(toluene sulfonate).

70. A process according to claim 63 wherein a Grignard reagent is also mixed in the liquid medium.

71. A process according to claim 70 wherein said Grignard reagent is phenylmagnesium halide.

72. A process according to claim 63 wherein said metal compound comprises a palladium compound.

73. A process according to claim 72 wherein said palladium compound is dipalladium tris(dibenzylideneacetone).

74. A process according to claim 64 wherein $R^1$ and $R^2$ of said N-heterocyclic carbene are the same, and each is a 2,4,6-trimethylphenyl group or a 2,6-diisopropylphenyl group, and wherein $R^3$ and $R^4$ of said N-heterocyclic carbene are the same, and each is a hydrogen atom.

75. A process according to claim 63 wherein the molar ratio of metal atoms of the metal compound to aryl pseudohalide molecules is in the range of from about 0.01:1 to about 0.05:1, and wherein the molar ratio of metal atoms of the metal compound to N-heterocyclic carbene is in the range of from about 1:0.5 to about 1:5.

* * * * *

UNITED STATES PATENT AND TRADEMARK OFFICE
CERTIFICATE OF CORRECTION

PATENT NO. : 6,369,265 B1
DATED : April 9, 2002
INVENTOR(S) : Steven P. Nolan et al.

It is certified that error appears in the above-identified patent and that said Letters Patent is hereby corrected as shown below:

Column 1,
Line 9, replace "filed Sep. 22, 1999." with -- filed Sep. 16, 1999. --.

Column 11,
Line 55, replace "bis(imidazoline2-ylidene)" with -- bis(imidazoline-2-ylidene) --.

Signed and Sealed this

Twenty-fourth Day of September, 2002

Attest:

JAMES E. ROGAN
Attesting Officer     Director of the United States Patent and Trademark Office